US00PP32729P2

(12) United States Plant Patent

Glawe et al.

(10) Patent No.: US PP32,729 P2
(45) Date of Patent: Jan. 5, 2021

(54) *PELARGONIUM* PLANT NAMED 'KLEPP20294'

(50) Latin Name: *Pelargonium peltatum*
Varietal Denomination: KLEPP20294

(71) Applicant: Klemm+Sohn GmbH & Co. KG, Stuttgart (DE)

(72) Inventors: Martin Glawe, Stuttgart (DE); Nina Neu, Murrhardt (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 16/871,016

(22) Filed: May 10, 2020

(51) Int. Cl.
*A01H 5/02* (2018.01)
*A01H 6/42* (2018.01)

(52) U.S. Cl.
USPC ..... Plt./328

(58) Field of Classification Search
USPC ..... Plt./324, 325, 328
See application file for complete search history.

*Primary Examiner* — Susan McCormick Ewoldt
(74) *Attorney, Agent, or Firm* — Weatherly IP Solutions, LLC; Barbara Campbell

(57) ABSTRACT

A new *Pelargonium* plant particularly distinguished by light blush pink flowers with red-purple centers, a bushy habit, and a trailing growth habit, is disclosed.

1 Drawing Sheet

Genus and species: *Pelargonium peltatum.*
Variety denomination: 'KLEPP20294'.

BACKGROUND OF THE NEW PLANT

The present invention comprises a new and distinct variety of *Pelargonium*, botanically known as *Pelargonium peltatum* and hereinafter referred to by the variety name 'KLEPP20294'. 'KLEPP20294' originated from a hand-pollination in July 2015 in Stuttgart, Germany between the female *Pelargonium* variety 'PP-2013-1007' (unpatented), and the male *Pelargonium* variety 'PP-2012-5017' (unpatented).

Seeds from the hand-pollination were obtained. The seeds were sown and plants were grown for evaluation. A single plant was selected in May 2016 and subsequently named 'KLEPP20294'. In July 2016, 'KLEPP20294' was first vegetatively propagated by vegetative stem cuttings. 'KLEPP20294' was found to reproduce true to type in successive generations of asexual propagation via vegetative cuttings in Stuttgart, Germany.

SUMMARY

The following are the most outstanding and distinguishing characteristics of this new variety when grown under normal horticultural practices in Stuttgart, Germany.

1. Light blush pink flowers with red-purple centers;
2. A bushy habit; and
3. A trailing growth habit.

DESCRIPTION OF THE PHOTOGRAPH

This new *Pelargonium* plant is illustrated by the accompanying photograph which shows an overall view of the plant. The photograph is of an approximately 12-week-old plant grown indoors in Stuttgart, Germany, in May 2019.

The colors shown are as true as can be reasonably obtained by conventional photographic procedures.

DESCRIPTION OF THE NEW VARIETY

The following detailed descriptions set forth the distinctive characteristics of 'KLEPP20294'. The data which define these characteristics were collected from asexual reproductions carried out in Stuttgart, Germany. Data was collected on 7-month-old plants in Stuttgart, Germany under greenhouse conditions in August 2019. Color references are to The R.H.S. Colour Chart of The Royal Horticultural Society of London (R.H.S.), 6$^{th}$ edition (2015).

Classification:
- *Family.*—Geraniaceae.
- *Botanical.—Pelargonium peltatum.*
- *Common.—Pelargonium.*
- *Designation.*—'KLEPP20294'.

Parentage:
- *Female parent.*—'PP-2013-1007' (unpatented).
- *Male parent.*—'PP-2012-5017' (unpatented).

Plant:
- *Form.*—Bushy.
- *Habit.*—Trailing.
- *Height (from top of soil).*—28.0 cm.
- *Width (horizontal plant diameter).*—30.0 cm.
- *Natural flowering season.*—April to October.
- *Propagation type.*—Vegetative stem cuttings.
- *Time to produce a finished flowering plant.*—12 weeks.
- *Time to initiate and develop roots.*—4 weeks.
- *Root description.*—Fine, dense, and RHS N155A (White).

Stems:
- *Quantity of stems per plant.*—12.
- *Color.*—RHS 143C (Green).
- *Surface texture.*—Pubescent, sparse.
- *Stem form.*—Round.
- *Diameter.*—0.4 cm.
- *Length.*—19.0 cm to 24.0 cm.
- *Internode length.*—2.2 cm.
- *Anthocyanin.*—Absent.

Leaves:
*Arrangement*.—Opposite.
*Shape*.—Spatulate.
*Apex*.—Acute.
*Base*.—Obtuse.
*Margin*.—Lobed.
*Depth of sinus*.—0.7 cm.
*Leaf blade base*.—Partly overlapping.
*Surface texture*.—Upper surface: Pubescent, sparse. Lower surface: Pubescent, sparse.
*Length*.—3.0 cm.
*Width*.—5.2 cm.
*Color*.—Upper surface: RHS 147A (Yellow-green). Lower surface: RHS 147B (Yellow-green).
*Petiole*.—Length: 3.3 cm. Diameter: 0.2 cm. Color: RHS 143A (Green). Strength: Medium.
*Venation pattern*.—Palmate.
*Venation color*.—Upper surface: RHS 147A (Yellow-green). Lower surface: RHS 143A (Green).
*Zonation*.—Present.
*Zone color*.—RHS 187A (Greyed-purple).
*Zone conspicuosness*.—Weak to medium.
*Zone position*.—Towards the base.
*Zone width*.—0.7 cm.

Inflorescence:
*Lastingness of flowers on the plant*.—6 to 8 days.
*Umbels*.—Quantity of umbels per plant: 40. Length: 4.1 cm. Diameter: 7.1 cm.
*Individual florets of the umbel*.—Quantity of florets per umbel: 6. Depth: 2.1 cm. Diameter: 4.4 cm.
*Fragrance*.—Absent.

Flower buds:
*Cluster shape*.—Elliptic.
*Cluster size*.—Length: 1.5 cm. Width: 0.7 cm.
*Surface texture*.—Pubescent, moderate.
*Bud*.—Height: 1.2 cm. Width: 0.6 cm. Shape: Elliptic. Apex: Acute. Base: Obtuse. Margin: Entire. Color: RHS 143B (Green).

Petals:
*Quantity per flower*.—12 to 14.
*Shape*.—Spatulate.
*Apex*.—Round.
*Base*.—Obtuse.
*Margin*.—Entire.
*Length*.—2.3 cm.
*Width*.—1.5 cm.
*Surface texture*.—Upper surface: Smooth. Lower surface: Smooth.
*Color of lobes*.—Upper lobes: Upper surface: The base color is RHS 75B (light Purple) with RHS N66B (Red-purple) centers. Lower surface: RHS 75D (light Purple). Lower lobes: Upper surface: The base color is RHS 75B (light Purple) with RHS N66B (Red-purple) centers. Lower surface: RHS 75D (light Purple).

Petaloids:
*Quantity per flower*.—0 to 2.
*Shape*.—Sometimes spatulate but mis-shaped with emarginate borders.
*Apex*.—Round.
*Base*.—Obtuse.
*Margin*.—Entire or emarginate.
*Length*.—1.7 cm.
*Width*.—0.7 cm.
*Surface texture*.—Upper surface: Smooth. Lower surface: Smooth.
*Color*.—Upper surface: The base color is RHS 75B (light Purple) with RHS N66B (Red-purple) centers. Lower surface: RHS 75D (light Purple).

Sepals:
*Number per flower*.—5.
*Shape*.—Elliptic.
*Apex*.—Acute.
*Base*.—Obtuse.
*Margin*.—Entire.
*Surface texture*.—Upper surface: Pubescent, moderate. Lower surface: Smooth.
*Color*.—Upper surface: RHS 143C (Green). Lower surface: RHS 143C (Green).
*Length*.—1.2 cm.
*Width*.—0.5 cm.

Pedicel:
*Length*.—2.0 cm.
*Diameter*.—0.1 cm.
*Color*.—RHS 143A (Green).
*Surface texture*.—Pubescent, sparse.
*Strength*.—Medium.

Peduncle:
*Length*.—9.2 cm.
*Diameter*.—0.3 cm.
*Color*.—RHS 143A (Green).
*Texture*.—Pubescent, sparse.
*Strength*.—Strong.

Reproductive organs:
*Stamens*.—Quantity per flower: 8. Anther length: 0.3 cm. Filament length: 0.3 cm. Filament color: RHS N155A (White). Pollen amount: Sparse. Pollen color: RHS 35A (Orange-red).
*Pistils*.—Number: 1. Stigma color: RHS 71A (Red-purple). Style length: 0.4 cm. Style color: RHS 157C (Green-white). Ovary arrangement: Central. Ovary color: RHS 141B (Green) but strongly pubescent; color of pubescence is RHS 157C (Green-white). Ovary diameter: 0.3 cm. Ovary length: 0.5 cm.

Fruit and seed set: None observed.
Disease and pest/insect resistance: None observed.

COMPARISON WITH PARENTAL LINE AND KNOWN VARIETY

'KLEPP20294' is distinguished from its female parent as described in Table 1. No information is available on the male parent.

TABLE 1

Comparison with Parental Line

| Characteristic | 'KLEPP20294' | Female parent 'PP-2013-1007' |
|---|---|---|
| Flower color | Bicolor | Single color, pink |
| Leaf zonation | Weak to medium | Absent |

'KLEPP20294' can be compared to the commercial variety PAC 'Vintage Rose' (patent status unknown). Differences between the two varieties are described in Table 2:

TABLE 2

Comparison with Similar Variety

| Characteristic | 'KLEPP20294' | PAC 'Vintage Rose' |
|---|---|---|
| Flower color | Light blush pink flowers with red-purple centers | Dark rose with purple blush |

We claim:

1. A new and distinct variety of *Pelargonium* plant named 'KLEPP20294' as illustrated and described herein.

* * * * *

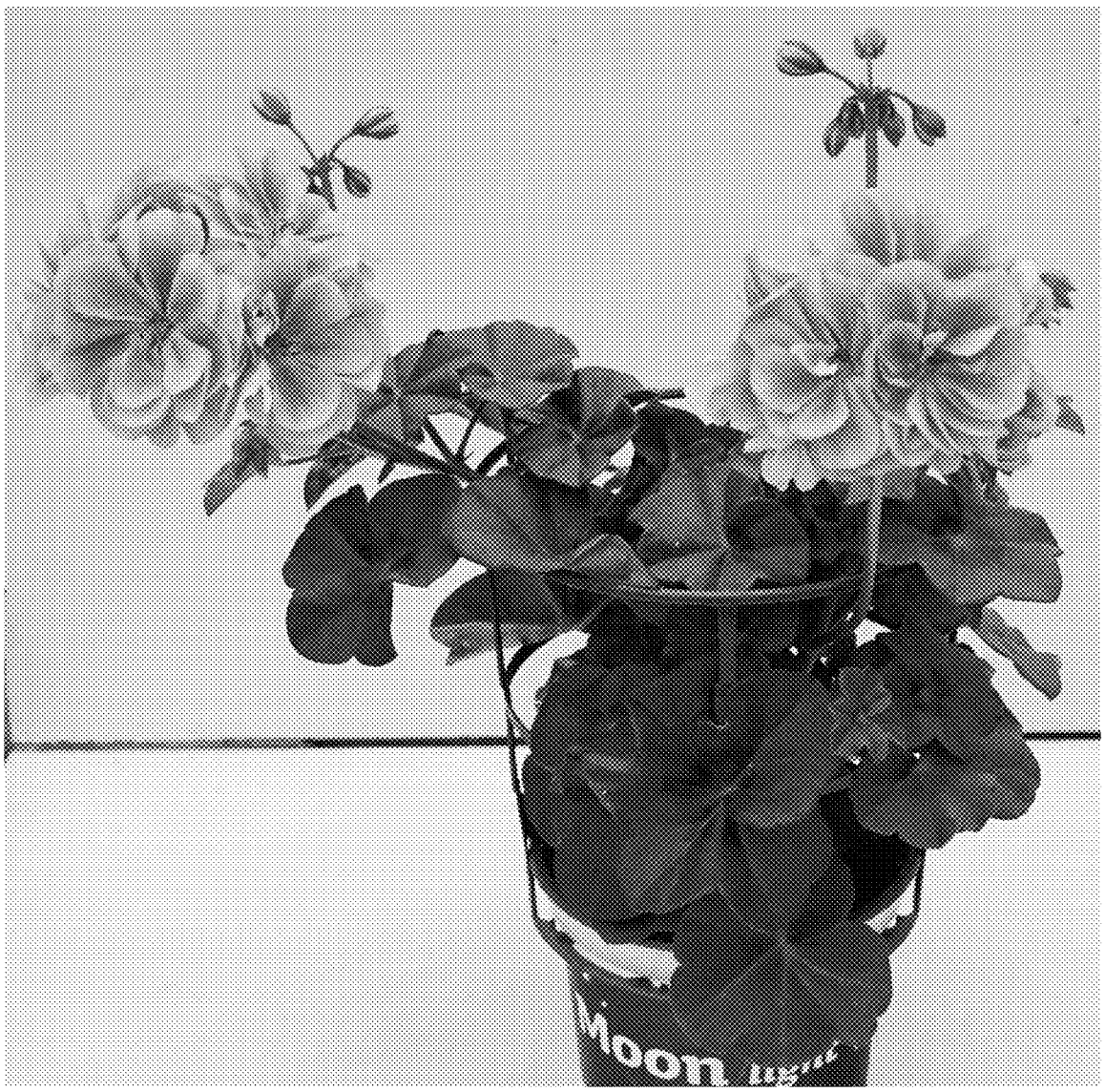
Moon